US009044347B2

(12) United States Patent
Cederna et al.

(10) Patent No.: US 9,044,347 B2

(45) Date of Patent: Jun. 2, 2015

(54) HYBRID BIOELECTRICAL INTERFACE DEVICE

(75) Inventors: Paul S. Cederna, Milan, MI (US); Brent M. Egeland, Ann Arbor, MI (US); Mohammad Reza Abidian, State College, PA (US); Antonio Peramo, Ann Arbor, MI (US); Melanie G. Urbanchek, Ann Arbor, MI (US); Daryl R. Kipke, Pinckney, MI (US); Sarah Richardson-Burns, Ann Arbor, MI (US); David C. Martin, Lincoln University, PA (US); Eugene D. Daneshvar, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 13/586,350

(22) Filed: Aug. 15, 2012

(65) Prior Publication Data

US 2014/0249645 A1 Sep. 4, 2014

Related U.S. Application Data

(63) Continuation of application No. 12/432,343, filed on Apr. 29, 2009, now abandoned.

(60) Provisional application No. 61/049,988, filed on May 2, 2008.

(51) Int. Cl.
*A61B 5/04* (2006.01)
*A61F 2/72* (2006.01)
(Continued)

(52) U.S. Cl.
CPC ... *A61F 2/72* (2013.01); *A61N 1/05* (2013.01); *A61N 1/0543* (2013.01);
(Continued)

(58) Field of Classification Search
USPC .............................................. 607/2, 115, 116
See application file for complete search history.

(56) References Cited

U.S. PATENT DOCUMENTS

| | | | |
|---|---|---|---|
| 4,341,221 | A | 7/1982 | Testerman |
| 4,585,652 | A | 4/1986 | Miller et al. |

(Continued)

FOREIGN PATENT DOCUMENTS

| | | | |
|---|---|---|---|
| WO | 97/16545 | A1 | 5/1997 |
| WO | 2007028003 | | 3/2007 |

(Continued)

OTHER PUBLICATIONS

Mohammad Reza Abidian and David C. Martini, Experimental and Theoretical Characterization of Implantable Neural Microelectrodes Modified with Conducting Polymer Nanotubes, Biiomaterials, vol. 29, 2008 (available online Dec. 18, 2008), p. 1273-1283.*

(Continued)

*Primary Examiner* — Carl H Layno
*Assistant Examiner* — Erica Lee
(74) *Attorney, Agent, or Firm* — Harness, Dickey & Pierce, P.L.C.

(57) ABSTRACT

A hybrid bioelectrical interface (HBI) device can be an implantable device comprising an abiotic component operable to transmit charge via electrons or ions; a biological component interfacing with the neural tissue, the biological component being sourced from biologic, biologically-derived, or bio-functionalized material; and a conjugated polymer component that together provide a way to chronically interface living neural tissue with electronic devices for extended durations (e.g. greater than 10 years). In some embodiments, conjugated polymers provide a functional electrical interface for charge transfer and signal transduction between the nervous system and an electronic device (e.g. robotic prosthetic limb, retinal implant, microchip).

16 Claims, 9 Drawing Sheets

A

B

(51) Int. Cl.

| | |
|---|---|
| ***A61N 1/05*** | (2006.01) |
| ***A61L 27/34*** | (2006.01) |
| ***A61L 27/36*** | (2006.01) |
| ***A61N 1/36*** | (2006.01) |

(52) U.S. Cl.

CPC ...... *A61N 1/0551* (2013.01); *A61F 2250/0001* (2013.01); *A61L 27/34* (2013.01); *A61L 27/3675* (2013.01); *A61N 1/36125* (2013.01)

(56) References Cited

U.S. PATENT DOCUMENTS

| | | | | |
|---|---|---|---|---|
| 4,662,884 | A | 5/1987 | Stensaas et al. | |
| 5,031,621 | A | 7/1991 | Grandjean et al. | |
| 5,092,332 | A | 3/1992 | Lee et al. | |
| 5,130,412 | A | 7/1992 | Wellinghoff et al. | |
| 5,368,028 | A | 11/1994 | Palti | |
| 5,513,636 | A | 5/1996 | Palti | |
| 5,540,734 | A | 7/1996 | Zabara | |
| 6,095,148 | A | 8/2000 | Shastri et al. | |
| 6,132,752 | A | 10/2000 | Pickett et al. | |
| 6,179,835 | B1 | 1/2001 | Panescu et al. | |
| 6,190,893 | B1 | 2/2001 | Shastri et al. | |
| 6,197,881 | B1 | 3/2001 | Cosnier | |
| 6,294,245 | B1 | 9/2001 | Roitman et al. | |
| 6,331,244 | B1 | 12/2001 | Lewis et al. | |
| 6,448,076 | B2 | 9/2002 | Dennis et al. | |
| 6,468,304 | B1 | 10/2002 | Dubois-Rande et al. | |
| 6,569,654 | B2 | 5/2003 | Shastri et al. | |
| 6,627,154 | B1 | 9/2003 | Goodman et al. | |
| 6,696,575 | B2 | 2/2004 | Schmidt et al. | |
| 6,730,212 | B1 | 5/2004 | Yamagishi et al. | |
| 6,890,715 | B1 | 5/2005 | Lewis et al. | |
| 7,045,205 | B1 | 5/2006 | Sager | |
| 7,070,592 | B2 | 7/2006 | Santini, Jr. et al. | |
| 7,120,486 | B2 | 10/2006 | Leuthardt et al. | |
| 7,147,865 | B2 | 12/2006 | Fishman et al. | |
| 7,181,288 | B1 | 2/2007 | Rezai et al. | |
| 7,233,097 | B2 | 6/2007 | Rosenthal et al. | |
| 7,708,908 | B2 | 5/2010 | Kim et al. | |
| 8,005,526 | B2 * | 8/2011 | Martin et al. ................. | 600/372 |
| 8,180,461 | B2 | 5/2012 | Mamo et al. | |
| 8,353,897 | B2 | 1/2013 | Doyle et al. | |
| 2005/0033132 | A1 | 2/2005 | Shults et al. | |
| 2005/0048651 | A1 | 3/2005 | Ryttsen et al. | |
| 2005/0121068 | A1 | 6/2005 | Sager et al. | |
| 2005/0234513 | A1 | 10/2005 | Alexander et al. | |
| 2005/0263394 | A1 | 12/2005 | Lewis et al. | |
| 2006/0057451 | A1 | 3/2006 | Okuzaki et al. | |
| 2006/0160100 | A1 | 7/2006 | Gao et al. | |
| 2007/0060815 | A1 * | 3/2007 | Martin et al. ................. | 600/372 |
| 2007/0073130 | A1 | 3/2007 | Finch et al. | |
| 2008/0097280 | A1 | 4/2008 | Martin et al. | |
| 2009/0118806 | A1 | 5/2009 | Vetter et al. | |
| 2009/0292325 | A1 | 11/2009 | Cederna et al. | |
| 2010/0211172 | A1 | 8/2010 | Bellamkonda et al. | |
| 2011/0087315 | A1 | 4/2011 | Richardson-Burns et al. | |
| 2012/0232630 | A1 | 9/2012 | Daneshvar | |
| 2013/0304174 | A1 | 11/2013 | Langhals et al. | |
| 2014/0005763 | A1 | 1/2014 | Cederna et al. | |

FOREIGN PATENT DOCUMENTS

| | | | |
|---|---|---|---|
| WO | 2008085199 | | 7/2008 |
| WO | 2010/011386 | A2 | 1/2010 |
| WO | 2011127166 | | 10/2011 |
| WO | 2012/097297 | A2 | 7/2012 |

OTHER PUBLICATIONS

Sarah M. Richardson-Burns et al., Polymerization of the Conducting Polymer Poly(3,4-ethylenedioxythiophene) (PEDOT) around Living Neural Cells, Biomaterials, vol. 28, 2007, p. 1539-1552.*

Abidian, M.R., et al., "Conducting-polymer nanotubes for controlled drug release," (2006), Advanced Materials, 18, pp. 405-409.

Campbell, T.E., et al., "Incorporation of Erythrocytes into Polypyrrole to Form the Basis of a Biosensor to Screen for Rhesus (D) Blood Groups and Rhesus (D) Antibodies," (1999), Electroanalysis, vol. 11, No. 4, pp. 215-222.

Chew, S.Y., et al., "Sustained Release of Proteins from Electrospun Biodegradable Fibers," (2005), Biomacromolecules, 6, pp. 2017-2024.

Cui, et al., "Surface modification of neural recording electrodes with conducting polymer/biomolecule blends," (2001), J. Biomed. Mater. Res., vol. 56, No. 2, pp. 261-272.

Cui, X., et al., "In vivo studies of polypyrrole/peptide coated neural probes," (2003), Biomaterials, 24, pp. 777-787.

Cui, X., et al., "Electrochemical deposition and characterization of conducting polymer polypyrrole/PSS on multichannel neural probes," (2001), Sensors and Actuators, A 93, pp. 8-18.

Cui, X., et al., "Electrochemical deposition and characterization of poly(3,4-ethylenedioxythiophene) on neural microelectrode arrays," (2003), Sensors and Actuators, B 89, pp. 92-102.

DiPaolo, B.C., et al., "Nanofiber scaffolding for improved neural electrode biocompatability," (2003), IEEE 29th Annual Conference, pp. 21-22.

Dong, H., et al., "Sub-Micrometer Conducting Polyaniline Tubes Prepared from Polymer Fiber Templates," (2004), Chem. Mater., 16, pp. 371-373.

Ghosh, S., et al., "Electrochemical Characterization of Poly(3,4-ethylene dioxythiophene) Based Conducting Hydrogel Networks," (2000) Journal of the Electrochemical Society, vol. 147, No. 5, pp. 1872-1877.

Gilmore, K., et al., "Preparation of Hydrogel/Conducting Polymer Composites," (1994), Polymer Gels and Networks, 2, pp. 135-143.

Gooding, J.J., et al., "Electrochemical modulation of antigent-antibody binding," (2004), Biosensors and Bioelectronics, 20, pp. 260-268.

Khor, E. et al., "In situ polymerization of pyrrole in animal tissue in the formation of hybrid biomaterials," (1995), Biomaterials, vol. 16, No. 8, pp. 657-661.

Kim, et al., "Incorporation and controlled release of a hydrophilic antibiotic using poly(lactide-co-glycolide)-based electrospun nanofibrous scaffolds," (2004), Journal of Controlled Release, 98, pp. 47-56.

Kim, B.C., et al., "Electroformation of conducting polymers in a hydrogel support matrix," (2000), Polymer, 41, pp. 1783-1790.

Kim, B.H., et al., "Synthesis, characteristics, and field emission of doped and de-doped polypyrrole, polyaniline, poly (3,4-ethylenedioxythiophene) nanotubes and nanowires," (2005), Synthetic Metals, 150, pp. 279-284.

Kim, D et al. "Conducting polymers grown in hydrogel scaffolds coated on neural prosthetic devices," (2004), J. Biomed. Mater. Res., 71A(4), pp. 577-585.

Kipke, D. R., et al., "Silicon-Substrate Intracortical Microelectrode Arrays for Long-Term Recording of Neuronal Spike Activity in Cerebral Cortex," (2003), IEEE Transactions on Neural Systems and Rehabilitation Engineering, vol. 11, No. 2, pp. 151-155.

Kositsky, M., et al., "Dynamical Dimension of a Hybrid Neurorobitic System," (2003), IEEE Transactions on Neural Systems and Rehabilitation Engineering, vol. 11, No. 2, only p. 155 available.

Nyberg, T., et al., "Polymer Hydrogel Microelectrodes for Neural Communication," (2002), Biomedical Microdevices vol. 4, No. 1, pp. 43-52.

Rahman, et al., "The biosensor based on the pyruvate oxidase modified conducting polymer for phosphate ions determinations," (2006), Biosensors and Bioelectronics, vol. 21, No. 7, pp. 1116-1124.

Schmidt, C.E., et al., "Stimulation of neurite outgrowth using an electrically conducting polymer," (Aug. 1997), Applied Biological Sciences: Proc. Natl. Acad. Sci. USA, vol. 94, pp. 8948-8953.

Supplementary European Search Report in PCT/US2006034199, mailed Mar. 9, 2010.

Woerly, S., "Restorative surgery of the central nervous system by means of tissue engineering using NeuroGel implants," (2000), Neurosurg Rev., 23, pp. 59-77.

(56) References Cited

OTHER PUBLICATIONS

Xiao, Y., et al., "Electrochemical polymerization of poly(hydroxymethylated-3,4-ethylenedioxythiophene) (PEDOT-MeOH) on multichannel neural probes," (2004), Sensors and Actuators, B 99, pp. 437-443.
Yang, J., et al., "Microporous conducting polymers on neural microelectrode arrays I. Electrochemical deposition," (2004), Sensors and Actuators, B 101, pp. 133-142.
Yang, J., et al., "Microporous conducting polymers on neural microelectrode arrays II Physical characterization," (2004), Sensors and Actuators, A 113, pp. 204-211.
Yang, J., et al., "Ordered surfactant-templated poly(3,4-ethylenedioxythiophene) (PEDOT) conducting polymer on microfabricated neural probes," (2005), Acta Biomaterialia, 1, pp. 125-136.
Zhang, Y., et al., "Recent development of polymer nanofibers for biomedical and biotechnological applications," (2005), Journal of Materials Science: Materials in Medicine, 16, pp. 933-946.
International Search Report and Written Opinion of the ISA for PCT/US2012/021311, ISA/KR, mailed Aug. 29, 2012.
International Preliminary Report on Patentability mailed on Jul. 16, 2013 for PCT International Application No. PCT/US2012/021311 (Pub. No. Wo 2012/097297).
International Search Report for PCT/US2009/042342, ISA/KR, mailed Feb. 5, 2010.
International Preliminary Report on Patentability mailed on Nov. 2, 2010 for PCT International Application No. PCT/US2009/042342 (Pub. No. Wo 2010/011386).
Abidian, M.R., et al., "Sensory Protection Recovery Follows Nerve Regeneration Through an Electrically Conducting Nerve Graft," 54th Annual Meeting, Plastic Surgery Research Council, May 27-30, 2009, Pittsburgh, PA, PSRC Abstract Supplement, vol. 126, No. 3 (Supplement), p. 40 (Jun. 2009) (Abstract only).
Aszmann, Oskar C., et al., "Evidence in Support of Collateral Sprouting After Sensory Nerve Resection," Annals of Plastic Surgery, vol. 37, No. 5, pp. 520-525 (1996).
Aszmann, Oskar C., et al., "Neuroma Prevention by End-to-Side Neurorraphy: An Experimental Study in Rats," Journal of Hand Surgery, vol. 28A, No. 6, pp. 1022-1028 (Nov. 2003).
Baghmanli, Ziya et al., "Impact of PEDOT on Peripheral Nerve Regeneration and Muscle Reinnervation," Plastic and Reconstructive Surgery, 70A, p. 52 (Jun. 2010 supplement).
Chandra, S., et al., "Proton-conducting gel electrolyte," Solid State Ionics, vol. 154-155, pp. 609-619 (2002).
Egeland, B.M., et al., "Biosynthetic Poly(3,4-ethylenedioxythiophene) (PEDOT) PNS Interfaces Can Deliver Afferent SNAPs With High Efficiency," American Society of Plastic Surgeons Meeting, Oct. 30-Nov. 6, 2008, Chicago, IL (Summary).
Egeland, B.M., et al., "Biosynthetic Poly(3,4-ethylenedioxythiophene) (PEDOT) PNS Interfaces Can Deliver Afferent SNAPs With High Efficiency," American Society for Peripheral Nerve Annual Scientific Meeting, Maui, HI, Jan. 11, 2009 (also presented at Annual Research Conference, Ann Arbor, MI, Mar. 2009) (Presentation).
Egeland, Brent M., et al., "In Vivo Electrical Conductivity across Critical Nerve Gaps Using Poly(3,4-ethylene-dioxythiophene)-Coated Neural Interfaces," Plastic and Reconstructive Surgery, vol. 126, No. 6, pp. 1865-1873 (Dec. 2010).
Egeland, Brent, et al., "In Vivo Electrophysiologic Properties of Poly 3,4-ethylene-dioxythiophene (PEDOT) in a Biosynthetic Nerve Interface," Midwestern Association of Plastic Surgeons, 48th Annual Scientific Meeting, May 4, 2008, Chicago, IL (Abstract and Presentation).
Egeland, Brent, et al., "In Vivo Electrophysiologic Properties of Poly (3,4-ethylene-dioxythiophene) PEDOT in Peripheral Motor Nerves," 54th Annual Meeting, Plastic Surgery Research Council, May 27-30, 2009, Pittsburgh, PA, PSRC Abstract Supplement, vol. 126, No. 3 (Supplement), p. 89 (Jun. 2009) (Abstract only).
Egeland, Brent M., et al., "Poly(3,4-ethylenedioxythiophene) PEDOT Bioengineered Constructs Can Deliver Afferent SNAPs With High Efficiency," American Society of Peripheral Nerve Annual Meeting, Jan. 6-9, 2009, Maui, HI (Presentation).
Egert, Daniel, et al., "New Class of Chronic Recording Multichannel Neural Probes With Post-Implant Self-Deployed Satellite Recording Sites," Solid-State Sensors, Actuators and Microsystems Conference (Transducers), Proceedings from IEEE 16th International Conference, Jun. 5-9, 2011, pp. 958-961.
Gao, Mei, et al., "Biosensors Based on Aligned Carbon Nanotubes Coated with Inherently Conducting Polymers," Electroanalysis, vol. 15, No. 13, pp. 1089-1094 (2003).
Heiduschka, P. et al., "Implantable Bioelectronic Interfaces for Lost Nerve Functions," Progress in Neurobiology, 1998, vol. 55, pp. 433-461.
Herr, Hugh, "New Horizons for Orthotic & Prosthetic Technology," Materials Research Society Spring Meeting, Symposium U: Advanced Materials for Neuroprosthetic Interfaces, Session U9: Integrated Designs and Devices, Apr. 12, 2007, San Francisco, CA (Oral Presentation) (Abstract only).
Jadcherla, Yamini, et al., "Nerve Regeneration through PEDOT, an Electrically Conducting Polymer Nerve Graft," Plastic and Reconstructive Surgery, vol. 124, No. 4 Supplement, p. 67 (Oct. 2009).
Kim, Dong-Hwan, "Effect of Immobilized Nerve Growth Factor on Conductive Polymers: Electrical Properties and Cellular Response," Advanced Functional Materials, vol. 17, pp. 79-86 (2007) (published online Nov. 20, 2006).
Lebedev, Mikhail, et al., "Brain-machine interfaces: past, present and future," Trends in Neurosciences, vol. 29, No. 9, pp. 536-546 (2006) (published online Jul. 21, 2006).
Lock, John P., et al., "Electrochemical investigation of PEDOT films deposited via CVD for electrochromic applications," Synthetic Metals, vol. 157, pp. 894-898 (2007) (published online Oct. 29, 2007).
Murji, A., et al., "The Role of Intraoperative Frozen Section Histology in Obstetrical Brachial Plexus Reconstruction" , J. Reconstr. Microsurg, 2008. 24(3): p. 203-209.
Nyberg, T., et al., Ion Conducting Polymer Microelectrodes for Interfacing with Neural Networks, Journal of Neuroscience Methods, vol. 160, 2007, pp. 16-25 (abstract only).
Peramo, Antonio, et a., "In Situ Polymerization of a Conductive Polymer in Acellular Muscle Tissue Constructs," Tissue Engineering: Part A, vol. 14, No. 3, pp. 423-432 (2008).
Pini, Niccolò, et al., "In situ growth of interdigitated electrodes made of polypyrrole for active fiber composites," Polymers for Advanced Technologies, vol. 18, pp. 249-253 (Mar. 2007) (published online Feb. 1, 2007).
Richardson-Burns, Sarah M. et al., "Electrochemical polymerization of conducting polymers in living neural tissue", J. Neural Eng. 4 (2007), L6-L13.
Smela, Elisabeth, "Conjugated Polymer Actuators for Biomedical Applications," Advanced Materials, vol. 15, No. 6, pp. 481-494 (Mar. 17, 2003).
Spinks, Geoffrey M., et al., "Actuation behaviour of layered composites of polyaniline, carbon nanotubes and polypyrrole," Synthetic Metals, vol. 151, pp. 85-91 (2005) (published online Jun. 13, 2005).
Talbi, H., et al., "Electropolymerization of aniline on carbonized polyacrylonitrile aerogel electrodes: applications for supercapacitors," Journal of Applied Electrochemistry, vol. 33, pp. 465-473 (2003).
Urbanchek, M.G., et al., "A Tissue-Based Bioelectrical Interface With Reduced Impedance Compared to Copper Wire and Nerve," 54th Annual Meeting, Plastic Surgery Research Council, May 27-30, 2009, Pittsburgh, PA, PSRC Abstract Supplement, vol. 126, No. 3 (Supplement), p. 26 (Jun. 2009) (Abstract only).
Urbanchek, M.G., et al., "Myoblast and Nerve Compatibility with PEDOT an Intrinsically Conductive Material," American Society of Plastic Surgeons Meeting, Nov. 2008, Chicago, IL (Presentation).
Urbanchek, M.G., et al., "Nerve Regeneration Through an Electrically Conducting Polymer Nerve Graft," 54th Annual Meeting, Plastic Surgery Research Council, May 27-30, 2009, Pittsburgh, PA, PSRC Abstract Supplement, vol. 126, No. 3 (Supplement), p. 90 (Jun. 2009) (Abstract only).
Watt, A.A.R., et al., "A PbS quantum-cube: conducting polymer composite for photovoltaic applications," Current Applied Physics, vol. 4, pp. 320-322 (2004).

* cited by examiner

HYBRID BIOELECTRICAL INTERFACE DEVICE

CROSS-REFERENCE TO RELATED APPLICATIONS

This application is a continuation of U.S. patent application Ser. No. 12/432,343 filed on Apr. 29, 2009. This application claims the benefit of U.S. Provisional Application No. 61/049,988 filed on May 2, 2008. The disclosure of the above referenced application is incorporated herein by reference.

GOVERNMENT INTEREST

This invention was made with government support under Grant No. W911NF0610218 awarded by the Army Research Office. The government has certain rights in the invention.

FIELD

The present technology relates to implantable hybrid bioelectrical interface devices that interface living neural tissue with artificial electronic components, in particular, neural-robotic bioelectrical coupling.

BACKGROUND SUMMARY

The statements in this section merely provide background information related to the present disclosure and may not constitute prior art.

Engineered limb prosthetics hold great potential for millions of spinal cord injury, neuromuscular disease, and amputation victims. Although sophisticated microelectronics and robotics facilitate ever closer approximations of human movement, interfacing the mechanical to the biological has proved challenging. Furthermore, providing graded sensory feedback from the prosthetic to the individual is critically important. Fundamentally, interface technologies must transduce neuron-based bioelectric action potentials saltatory conduction along myelinated axons mediated by mass transfer (ion currents) directly or indirectly to an electrical current through a metallic conductor. Multiple studies have dramatically demonstrated volitional prosthetic control using implanted cortical electrodes in primate models. With these successful demonstrations, the practical aspects of using central neural electrodes for human deployment including their surgical invasiveness, biofouling, encapsulation, foreign body response, and reliance on capacitive and high impedance electronics—all which lead to time-related signal degradation—become foremost challenges.

To avoid some of these obstacles, natural functional and anatomic separation of axons into fascicles in the peripheral nervous system may provide a more attractive interface site. Indeed, neurotization, or targeted muscle reinnervation procedures exploit peripheral nerve sorting, biologic plasticity, and ultimately, neuromuscular junction stability. Expanding this concept to human volitional prosthetic control, some in the field have recently demonstrated that Targeted Muscle Reinnervation (TMR), or independent reinnervation of several individual muscle partitions by isolated nerves (from the brachial plexus), could indirectly drive a robotic prosthetic through surface EMG (electromyography) recordings. These exciting clinical results are already being deployed in select patients, but donor muscle limitations and reliance on non-integrated surface EMG may preclude achieving individual axonal fidelity (i.e. proximal interphalangeal joint flexion of the index finger), and sensory feedback has only been partially addressed.

SUMMARY

In one aspect of the present technology, hybrid bioelectrical interface (HBI) devices for interfacing living neural tissue with electronic devices comprises: an abiotic component operable to transmit charge via electrons or ions; a biological component interfacing with the neural tissue, the biological component being sourced from biologic, biologically-derived, or bio-functionalized material; and a conjugated polymer component interfacing the abiotic component and the biological component, such that the conjugated polymer component promotes electronic to ionic charge transfer between the abiotic and biotic components.

In a further aspect, the hybrid bioelectrical interface (HBI) devices comprise a housing providing for coordinated and structural direction for nerves to be interfaced with synthetic neural devices and artificial prostheses. The hybrid bioelectrical interface (HBI) devices can include a housing made from a polymer material such as polydimethylsiloxane (PDMS) or a hydrogel material, for example, agarose. The housing can contain a structural framework to provide rigidity, support and improved handling characteristics for the housing and the components contained therein. The housing surrounds a biological component that is interfaced with conjugated polymer. The conjugated polymer in turn, interfaces with an abiotic component and a biological component. The conjugated polymer component and biological components can be covered or surrounded by the housing.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1A depicts a graphical representation of an illustrative embodiment of the implantable hybrid bioelectrical interface device showing in partial exploded view the various components of the hybrid bioelectrical interface device in accordance with the present technology.

FIG. 1B depicts a graphical representation of an illustrative embodiment of the implantable hybrid bioelectrical interface device showing in cross-sectional view the distal portion of the hybrid bioelectrical interface device illustrating a plurality of abiotic electrodes held by a surrounding framework in proximate contact with the biological component (myocytes) for recording and/or stimulating action potentials through a conducting polymer within the length of the device in accordance with the present technology.

FIG. 2 depicts the manufacture of two hybrid bioelectrical interface devices having in which the abiotic component is a cluster of microwires connected to an EED (FIG. 2, A), the biotic component is either an acellularized tissue scaffold or a naturally based hydrogel scaffold both of which can be seeded with dissociated skeletal muscle cells (FIG. 2, B), the conjugated polymer component is either a PEDOT-coated acellularized tissue scaffold or in situ polymerized PEDOT that is polymerized directly within the either acellularized tissue scaffold or naturally based hydrogel scaffold seeded with living muscle cells (FIGS. 2, D&H), the container is a tubular polymer membrane that is filled with a hydrogel matrix which serves as an electrolytes as well as a structural and nutritive support for the muscle cells and implanted nerve (FIGS. 2, G&J). The proximal end of a single motor nerve fascicle is inserted into the open end of the hybrid bioelectrical interface device so that it contacts the muscle cells and the conjugated polymer component of the device.

FIG. 3A depicts a hybrid bioelectrical interface device for in vitro studies. The abiotic component is interfaced with acellularized muscle tissue having PEDOT conjugated polymer disposed within. Neural structures have formed neuromuscular junctions with the myocytes to form myotubes in the acellular muscle tissue.

Figure 4:
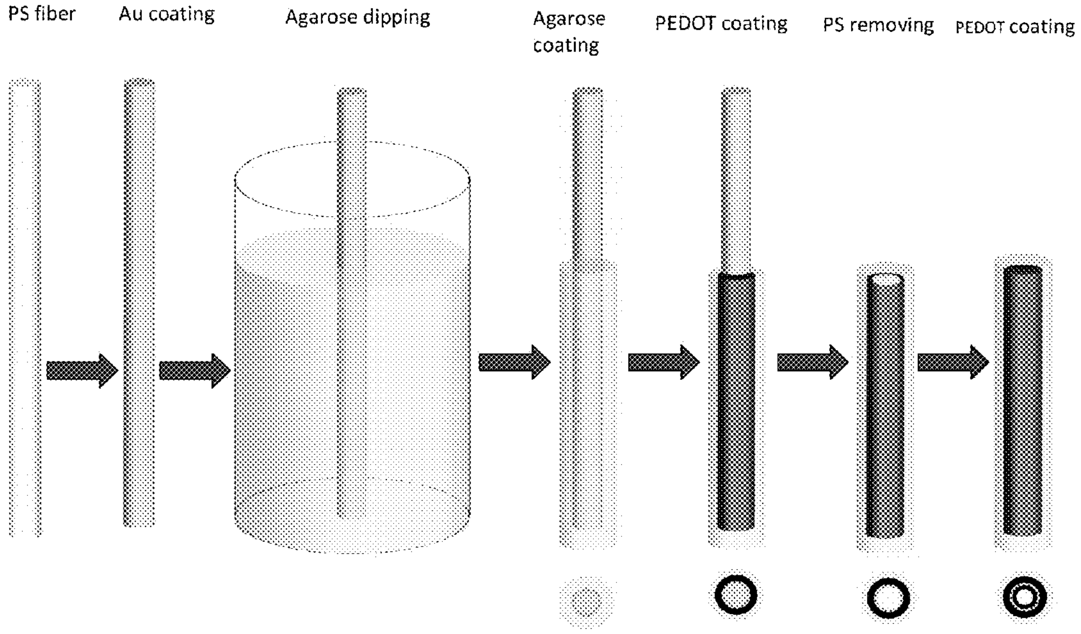
FIG. 4 depicts a graphical representation of the process steps in fabricating an embodiment of the hybrid bioelectrical interface device using a housing consisting of agarose in accordance with the present technology.
Figure 5:
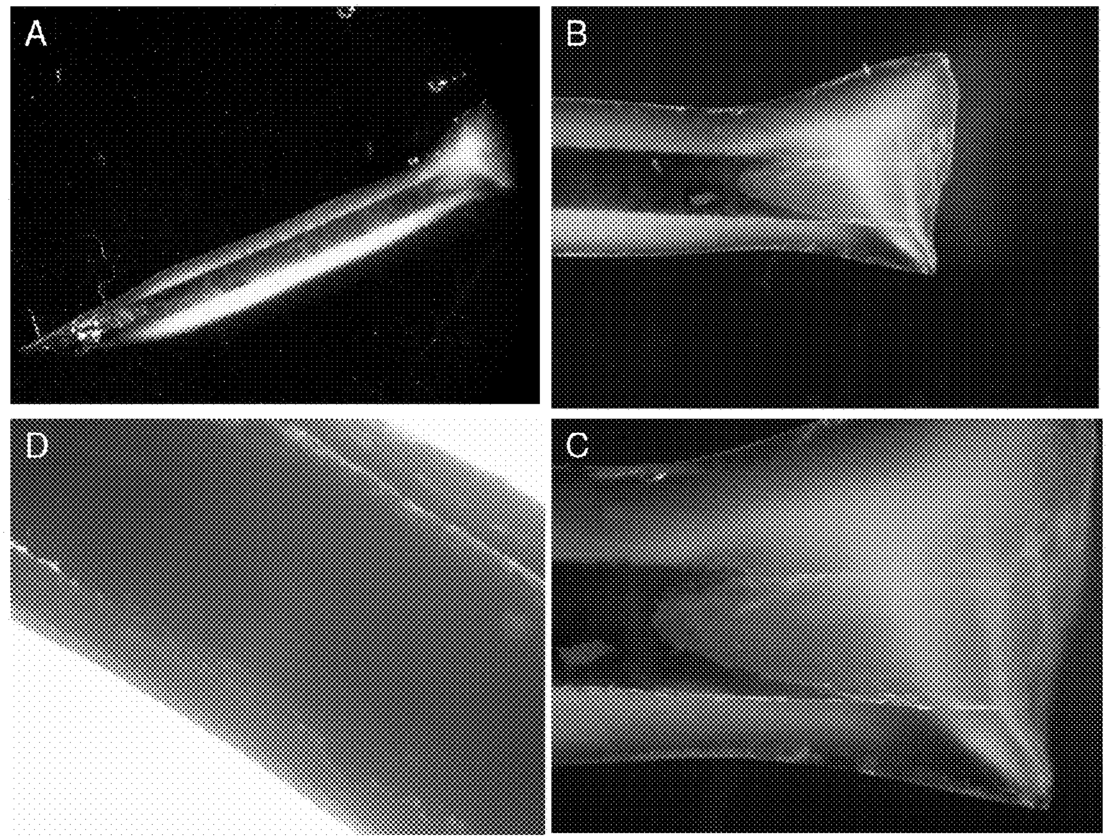

FIG. 5A is a optical microphotograph of a hydrogel housing surrounding a poly(3,4-ethylenedioxythiophene) (PEDOT) conjugated polymer cylinder as graphically represented in FIG. 4. The inset represents the distal end of the hybrid bioelectrical interface device. As shown in FIG. 6A-6C, the insets are reproduced in magnified form as marked by the dotted lines.

FIG. 5B is a magnified optical micrograph of the inset shown in FIG. 5A depicting the distal end of the hybrid bioelectrical interface device. The inset represents a magnified portion of the distal end of the hybrid bioelectrical interface device in accordance with the present technology.

FIG. 5C is a magnified optical micrograph of the inset shown in FIG. 5B depicting the distal end of the hybrid bioelectrical interface device. The inset represents a portion of the poly(3,4-ethylenedioxythiophene) (PEDOT) conjugated polymer cylinder in accordance with the present technology.

FIG. 5D is a magnified optical micrograph of the inset shown in FIG. 5C a portion of the poly(3,4-ethylenedioxythiophene) (PEDOT) conjugated polymer cylinder in accordance with the present technology.

FIG. 6A depicts a graphical representation of an embodiment of the hybrid bioelectrical interface device. The housing made from agarose covers a framework (stainless steel stent) partially disposed from the distal and proximal ends towards the center of the device. A cylindrical tube made up entirely of poly(3,4-ethylenedioxythiophene) (PEDOT) is formed in the middle of the HBI device housing within the stainless steel stent.

FIG. 6B depicts a graphical representation of an embodiment of the hybrid bioelectrical interface device. The housing and center portion of the device is made from agarose. A stainless steel stent is inserted into the agarose partially disposed from the distal and proximal ends towards the center of the device.

FIG. 6C depicts a graphical representation of an embodiment of the hybrid bioelectrical interface device. The housing made from agarose covers a stainless steel stent partially disposed from the distal and proximal ends towards the center of the device. A spiral cylindrical tube made up of poly(3,4-ethylenedioxythiophene) (PEDOT) is formed in the middle of the device within the stainless steel stent.

FIG. 6D depicts a graphical representation of an embodiment of the hybrid bioelectrical interface device. The housing made from agarose covers a polydimethylsiloxane (PDMS) cylindrical tube.

Figure 7:
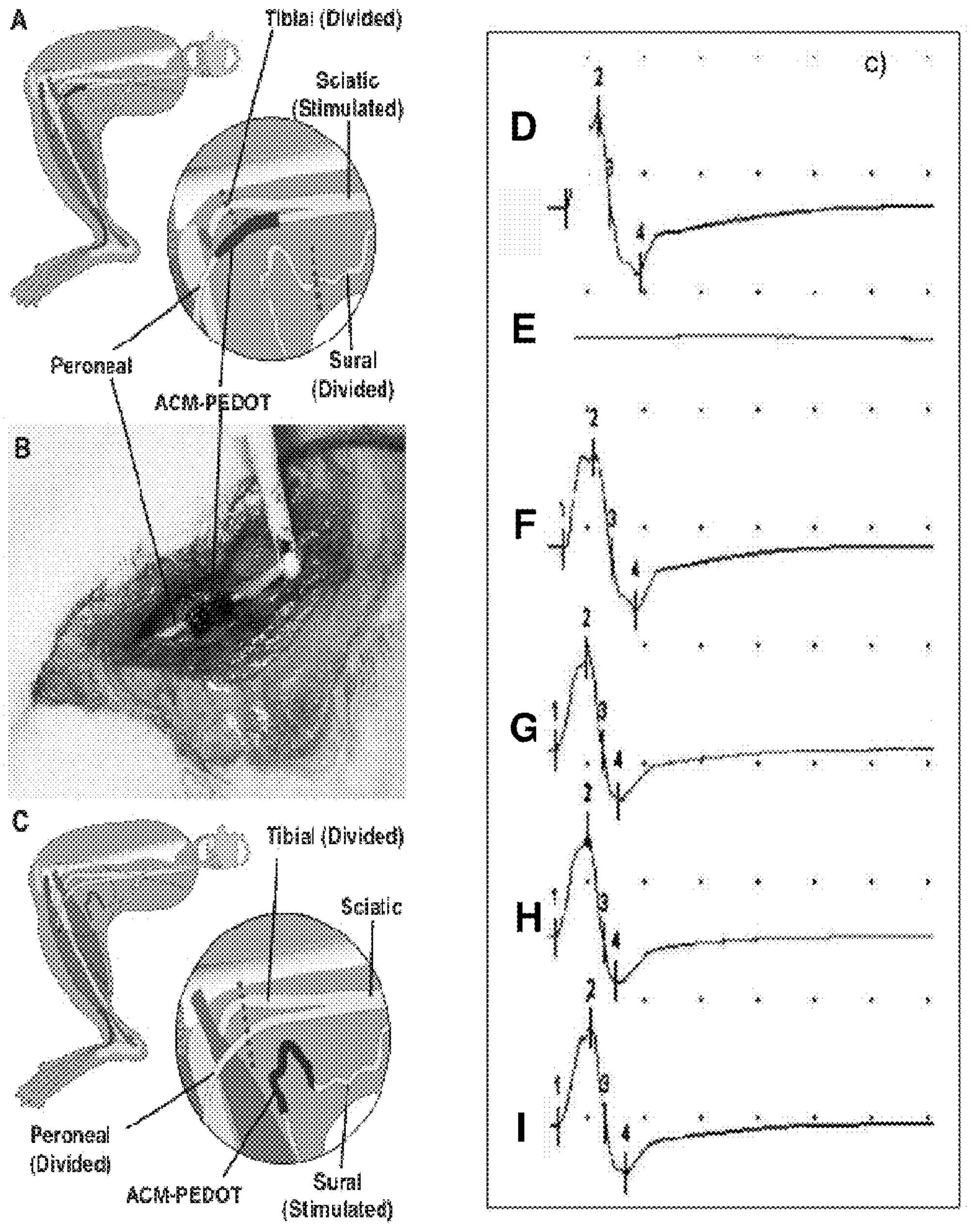

FIG. 7A depicts a schematic representation demonstrating mid-peroneal nerve interposition using the hybrid bioelectrical device in vivo for purposes of bridging a critical efferent motor conduction gap. Other neural pathways are divided to isolate the efferent pathway.

FIG. 7B is a photograph of the peroneal nerve interposed with the hybrid bioelectrical device and prepared for efferent recording of stimulation applied proximally to the sciatic nerve and distally recording transmitted action potentials.

FIG. 7C depicts a schematic representation demonstrating mid-sural nerve interposition using the hybrid bioelectrical device in vivo for purposes of bridging a critical afferent sensory conduction gap. For afferent experiments, the sural nerve from a rat model was isolated by dividing the tibial and peroneal nerves, followed by antidromic sensory electrodiagnostic studies.

FIG. 7D depicts a electromyography trace of an intact nerve signaling efferent (motor) nerve action potentials.

FIG. 7E depicts a electromyography trace of proximal nerve conduction of efferent (motor) nerve action potentials following nerve division preceding interposition of the hybrid bioelectrical interface device.

FIG. 7F depicts a maintained electromyography trace of distal nerve conduction of efferent (motor) nerve action potentials following nerve division preceding interposition of the hybrid bioelectrical interface device.

FIG. 7G. depicts a electromyography trace of nerve conduction of efferent (motor) nerve action potentials applied across the hybrid bioelectrical interface device made with acellular muscle framework having poly(3,4-ethylenedioxythiophene) (PEDOT) dispersed throughout the acellular muscle. This represents successful electrical signal delivery across a critical conduction gap in vivo.

FIG. 7H depicts a electromyography trace of nerve conduction of efferent (motor) nerve action potentials wherein the stimulation is applied directly to the hybrid bioelectrical interface device made with acellular muscle having poly(3,4-ethylenedioxythiophene) (PEDOT).

FIG. 7I depicts a electromyography trace of an intact nerve signaling efferent (motor) nerve action potentials stimulated and recorded at a distal position to the hybrid bioelectrical interface device made with acellular muscle having poly(3,4-ethylenedioxythiophene) (PEDOT) dispersed throughout the acellular muscle.

Figure 8:
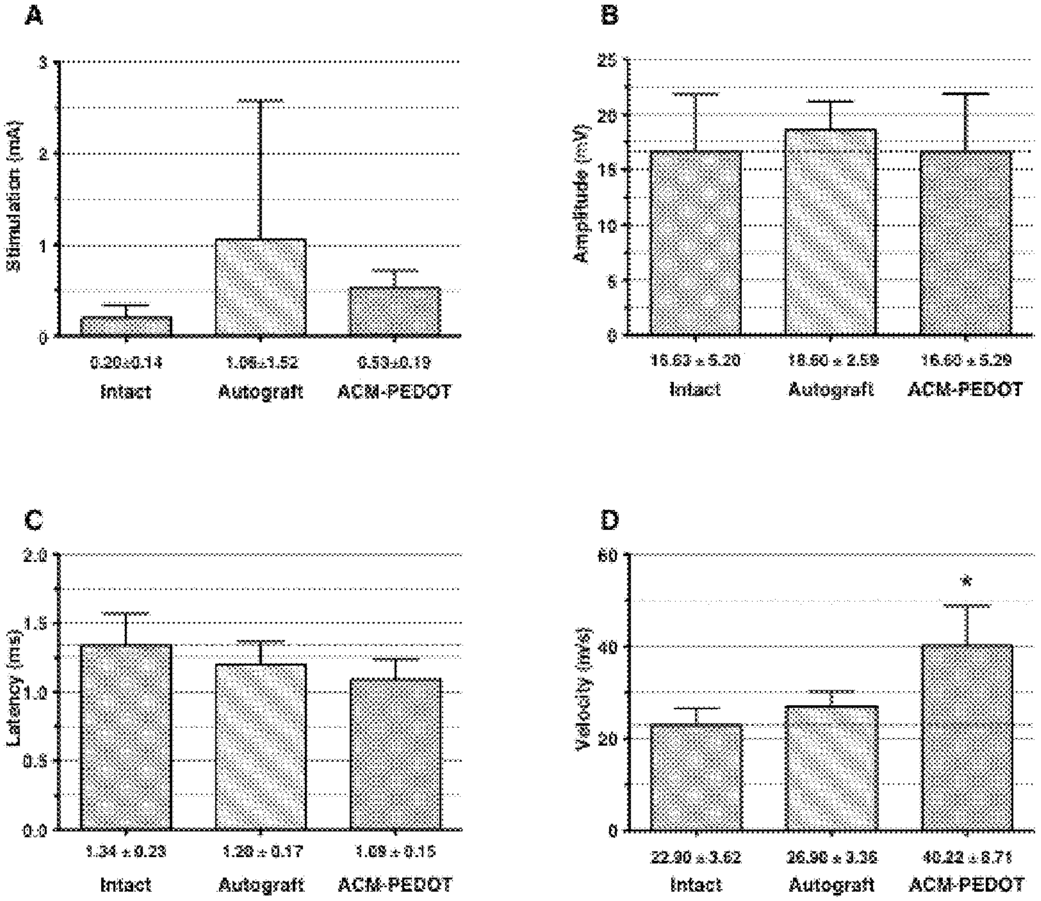

FIG. 8A depicts a bar graph depicting efferent nerve conduction across the peroneal nerve. The bar graphs depict the results of measured current (mA) delivered directly to: 1) intact peroneal nerve, 2) nerve interposited with an autograft of rat nerve measuring 20 mm and nerve interposited with the hybrid bioelectrical device measuring 20 mm.

FIG. 8B depicts a bar graph depicting efferent nerve conduction across the peroneal nerve. The bar graphs depicts the results of measured compound muscle action potential amplitude (millivolts) recorded at a point of musculature distal to point of stimulation in three nerve constructs, 1) intact peroneal nerve, 2) nerve interposited with an autograft of rat nerve measuring 20 mm and nerve interposited with the hybrid bioelectrical device measuring 20 mm.

FIG. 8C depicts a bar graph depicting efferent nerve conduction across the peroneal nerve. The bar graphs depicts the results of measured nerve conduction latency (milliseconds) recorded at a point of musculature distal to point of stimulation in three nerve constructs, 1) intact peroneal nerve, 2)

nerve interposited with an autograft of rat nerve measuring 20 mm and nerve interposited with the hybrid bioelectrical device measuring 20 mm.

FIG. 8D depicts a bar graph depicting efferent nerve conduction across the peroneal nerve. The bar graphs depicts the results of measured nerve conduction velocity (meters per second) recorded at a point of musculature distal to point of stimulation in three nerve constructs, 1) intact peroneal nerve, 2) nerve interposited with an autograft of rat nerve measuring 20 mm and nerve interposited with the hybrid bioelectrical device measuring 20 mm.

Figure 9:
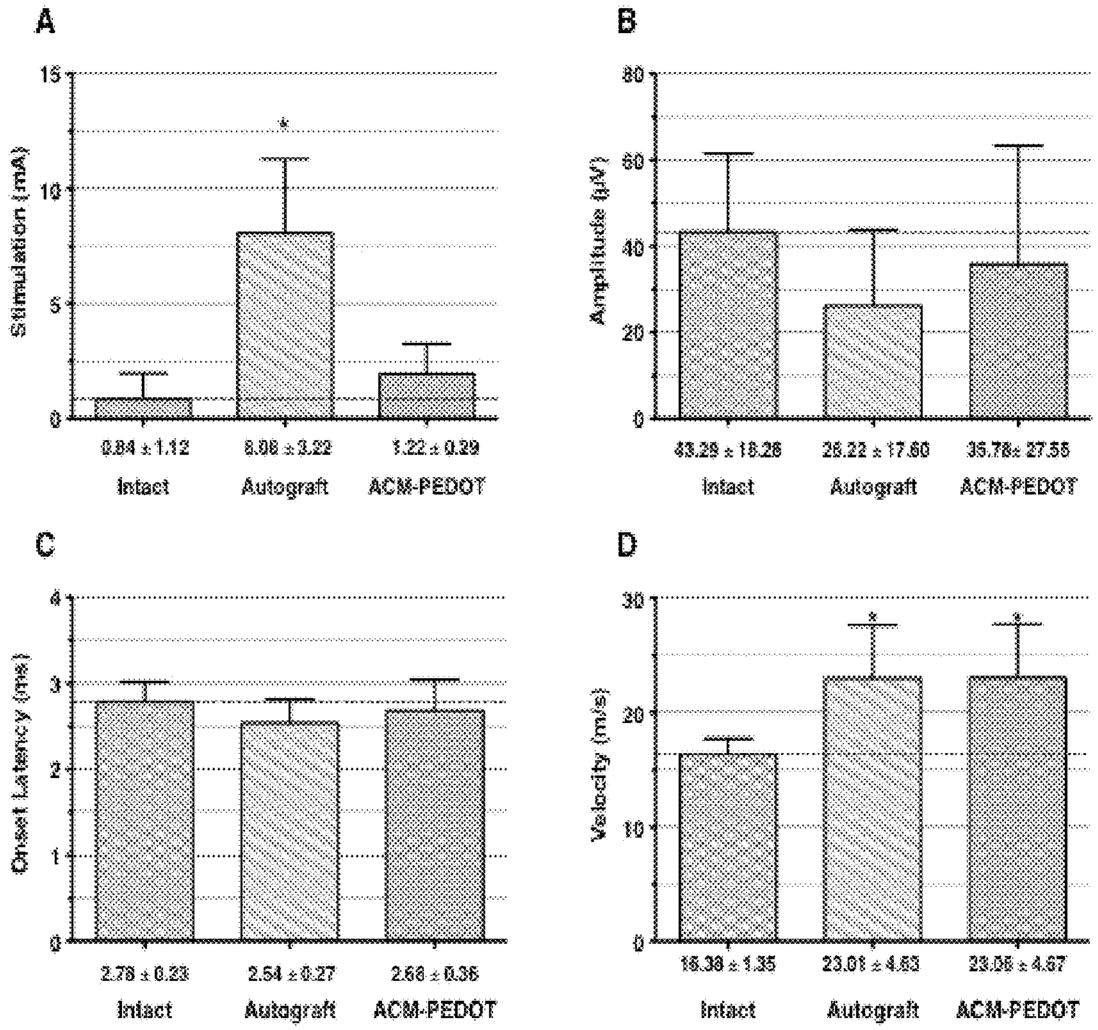

FIG. 9A depicts a bar graph depicting afferent sensory nerve action potentials (SNAPs) for signal propagation across the sural nerve. The bar graphs depict the results of current (mA) delivered directly to, the sural nerve proximal to the point of recording (antidromic schema) in three constructs, 1) intact sural nerve, 2) nerve interposited with an autograft of rat nerve measuring 20 mm and nerve interposited with the hybrid bioelectrical device measuring 20 mm.

FIG. 9B depicts a bar graph depicting antidromic afferent sensory nerve action potentials (SNAPs) for signal propagation across the sural nerve. The bar graphs depicts the results of measured sensory nerve action potential amplitude (millivolts) recorded at a nerve site distal to the point of stimulation in three nerve constructs, 1) intact sural nerve, 2) nerve interposited with an autograft of rat nerve measuring 20 mm and 3) nerve interposited with the hybrid bioelectrical device measuring 20 mm.

FIG. 9C depicts a bar graph depicting antidromic afferent sensory nerve action potentials (SNAPs) for signal propagation across the sural nerve. The bar graphs depicts the results of measured sensory nerve conduction latency (milliseconds) recorded at a nerve site distal to the point of stimulation in three nerve constructs, 1) intact sural nerve, 2) nerve interposited with an autograft of rat nerve measuring 20 mm and 3) nerve interposited with the hybrid bioelectrical device measuring 20 mm.

FIG. 9D depicts a bar graph depicting antidromic afferent sensory nerve action potentials (SNAPs) for signal propagation across the sural nerve. The bar graphs depicts the results of measured sensory nerve conduction velocity (meters per second) recorded at a nerve site distal to the point of stimulation in three nerve constructs, 1) intact sural nerve, 2) nerve interposited with an autograft of rat nerve measuring 20 mm and 3) nerve interposited with the hybrid bioelectrical device measuring 20 mm.

DETAILED DESCRIPTION

The following description is merely exemplary in nature and is not intended to limit the present disclosure, application, or uses.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

According to the principles of the present technology, the hybrid bioelectrical interface device (HBI) device can be an implantable device comprising interacting synthetic/natural materials, biological components, and abiotic devices that together provide a means to chronically interface living neural tissue with electronic devices for extended durations (e.g. 1-100 years). In some embodiments, conjugated polymers provide a functional electrical interface for charge transfer and signal transduction between the nervous system and an electronic device (e.g. an electrode, robotic prosthetic limb, retinal implant and microchip). In addition, the conjugated polymers can be disposed in and around a biological component. The biological component can be coupled to electrically active biological components such as nerve constituents, nerve fascicles, neurons, myocytes, cardiomyocytes, and other biological cells and structures that can conduct an afferent and/or efferent electrical signal. The conjugated polymer component can also undergo a change in bias upon electrical or electronic stimulation that can result in actuation, effectively a reversible volume change in the polymer matrix and/or ion flux with the surrounding electrolyte medium. This behavior of the conjugated polymer can be exploited to provide controlled release of the materials, molecules, or devices incorporated into the conjugated polymer matrix or into the conjugated polymer substrate as a form of drug or biologically active agent, for example, adhesion molecules, chemotactic agent growth factor delivery.

A. Hybrid Bioelectrical Interface (HBI) Device

Figure 1:
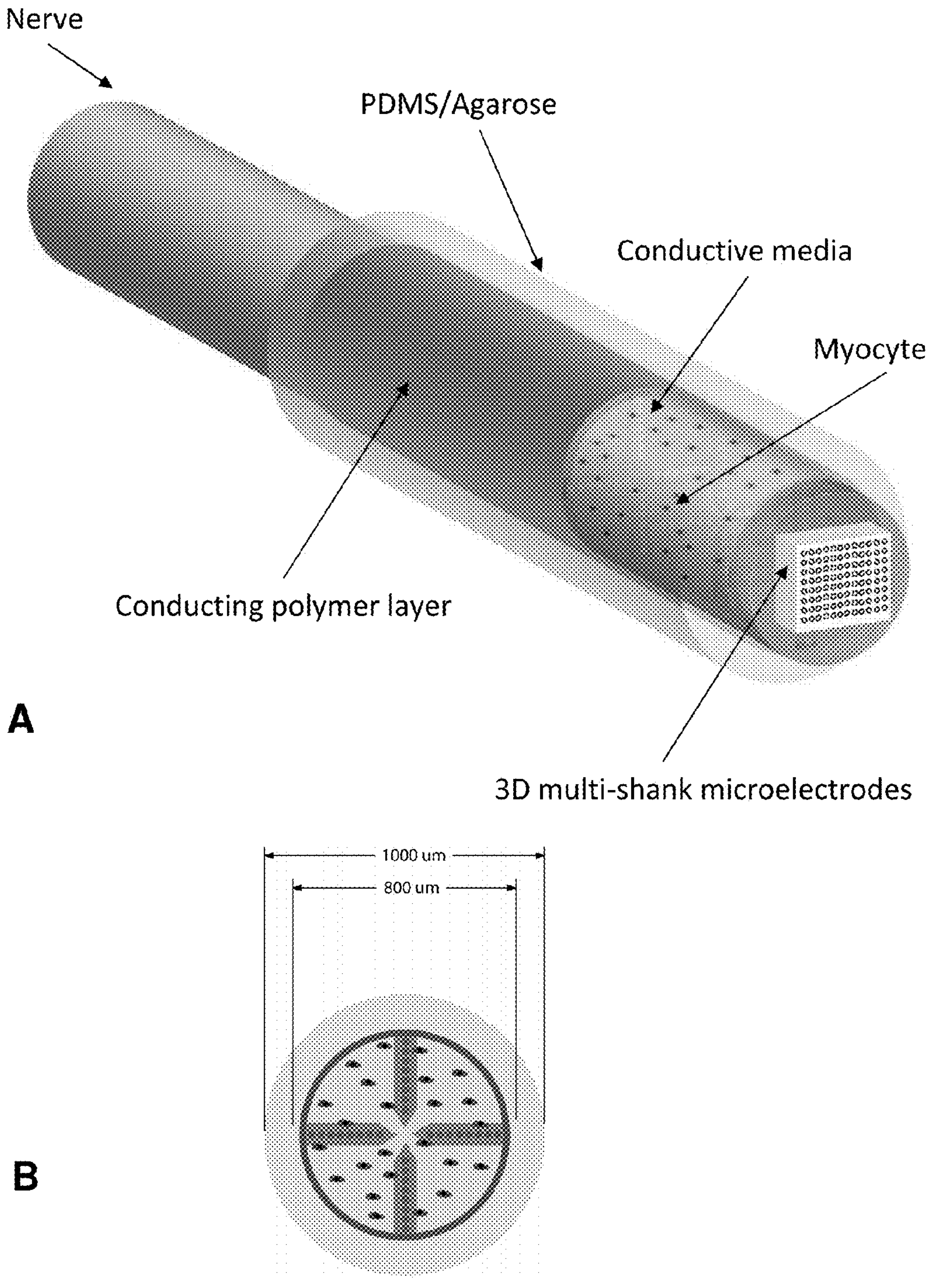

The technology described herein relates to a bio-artificial neuromuscular interface herein termed a hybrid bioelectrical interface device (HBI) that is illustratively shown in FIG. 1. The HBI device is an implantable device that provides a functional, electrical interface between an external electronic device (EED) and an electrically-active tissue such as the sensory nerves, motor nerves or cardiac tissue. In some embodiments, the present technology described herein provides an HBI device having an abiotic component intended for long-term implantation in the body, however in some embodiments the HBI device can be deployed outside the body as long as it is still connected to the electronic prosthetic device. A chronic interface with the peripheral nervous system that allows for recording as well as stimulation, opens the door to a number of new devices and treatments. The HBI device performs electronic and/or ionic charge transfer and bi-directional signal transduction between neural tissue and an abiotic component through a conjugated polymer such as poly (3,4-ethylenedioxythiophene) PEDOT. The central component of the HBI is a conjugated polymer coating, network, or scaffold that can have functional contact on one end with an abiotic component, for example, an electrode which connects to an EED and on the other end with cells, tissue, a biological material, or a biomimetic or bio-functionalized material that has a functional interface with the neural tissue. The HBI device can be used to perform one or both of the following functions; 1) send signals and information (e.g. electrical stimulation, deliver bioactive agents) and 2) receive information (e.g. monitoring/sensing, recording, or transduction of signal to EED).

Various embodiments of the HBI device are illustratively shown in the present disclosure in FIGS. 1-3B, however, the HBI device is not limited to these embodiments, and one of ordinary skill in the art can readily ascertain different embodiments containing the same major components. However, many have similar functions and major components. These components include 1) An abiotic component such as a wire, microelectrode array, electrode, a microelectromechanical system, or any other artificial, synthetic electronic component that transmits charge via electrons or ions. In some embodiments an electrode can be directly connected to the EED. 2) A biological or biologically derived or bio-functionalized component which interfaces the electrically active tissue. 3) A conjugated polymer component that interfaces both the abiotic component and the biological component facilitating and/or enhancing electronic to ionic charge transfer between the abiotic and biological components of the device. 4) Optionally, a housing, for example, a membrane, polymer or hydrogel microtube within which the biological component and conjugated polymer and other components of the HBI device are housed, making the HBI device a self-contained device that can be implanted in a body, for coordinated neural growth and innervation within the device and for connectivity with electronic devices and prosthetic limbs. The HBI may have multiple abiotic, biological and conjugated polymer components but must contain at least one of each. It should be appreciated, however, that variations can exist between the disclosed embodiments and their specific components and alternative embodiments that are intended to be within the scope of the present application.

I) Abiotic Conductor Component

The abiotic conductor can include metallic, ceramic, organic and silicon containing materials and devices that are capable of conducting stimulatory and sensory electrical, ionic, electronic, mechanical, physical, magnetic e.g. pulsed electromagnetic, acoustic and optical signals in vivo and in vitro. These components can include a host of electrical sensing and recording components, including metal wires, plain metal electrodes, ceramic and/or polymer patterned electrodes, microelectrode arrays, electrode arrays and microelectrodes. Electrodes can incorporate substrates having any conducting material or combination of conducting and non-conducting materials. A number of exemplary electrically conductive substrate configurations are described and can be understood that other configurations can be used. In non-limiting embodiments, electrically conductive substrates can be manufactured from metals including, but not limited to: Gold (Au), Platinum (Pt), Iridium (Ir), Palladium (Pd), Tungsten (W), Nickel (Ni), Copper (Cu) Aluminum (Al), Stainless Steel (SS), Indium-Tin-Oxide (ITO), Zinc (Zn), Titanium (Ti), Tungsten (W) and their alloys and oxides. Other electrically conductive substrates can include: carbon, carbon fiber, glassy carbon, carbon composites, carbon paste, conductive ceramics, for example, doped silicon (Si), conductive monomers and polymers, e.g. poly(3,4-ethylenedioxythiophene) (PEDOT) and poly(pyrrole).

Abiotic components comprising one or more electrode arrays can include any suitable support material upon which a plurality of conducting material channels, dots, spots are formed. In general, if the support material of the electrode is to come into contact with biological fluid, the support should be essentially biocompatible. The microelectrode arrays of the present technology need not be in any specific shape, that is, the electrodes need not be in a square matrix shape. Contemplated electrode array geometries can include: squares; rectangles; rectilinear and hexagonal grid arrays various polygon boundaries; concentric circle grid geometries wherein the electrodes form concentric circles about a common center, and which may be bounded by an arbitrary polygon; and fractal grid array geometries having electrodes with the same or different diameters. Interlaced electrodes can also be used in accordance with the present technology. In some embodiments, the array of electrodes can comprise about 9 to about 16 electrodes in a 4×4 matrix, 16 to about 25 electrodes in about a 5×5 matrix, 10 to 100 electrodes in a 10×10 matrix. Other sized arrays, for example polymer based Michigan and Utah electrodes known in the art may be used in accordance with the present technology.

Production of patterned array of microelectrodes can be achieved by a variety of microprinting methodologies commonly known in the production of micro-arrays, including, without limitation, by ejecting a plurality of electro-conducting polymers via a multi-line head nozzle, via ink-jetting techniques and the like. They can be patterned using photolithographic and etching methods known for computer chip manufacture. The micromechanical components may be fabricated using compatible "micromachining" processes that selectively etch away parts of the silicon wafer, or comparable substrate, or add new structural layers to form the mechanical and/or electromechanical components.

Micro-electro-mechanical systems (MEMS) based electrodes formed on polymeric supports such as those contemplated in Micro-electro-mechanical systems (MEMS) manufacture can include depositing thin films of conducting material on a support material, applying a patterned mask on top of the films by photolithographic imaging or other known lithographic methods, and selectively etching the films. A thin film may have a thickness in the range of a few nanometers to 100 micrometers. Deposition of electroconducting materials for use as micro or nano electrodes contemplated in the present technology can also include chemical procedures such as chemical vapor deposition (CVD), electrodeposition, epitaxy and thermal oxidation and physical procedures like physical vapor deposition (PVD) and casting.

II) Biological Component

As used herein, the biological component of the present technology can in non-limiting examples, include autologous, allogous or allogeneic or xenogeneic tissue, preferably, tissue capable of supporting the growth of neural tissue, including neurons and substructures thereof, skeletal muscle, cardiac muscle, smooth muscle, and cells thereof. In some embodiments, the biological component can contain a plurality of cells derived from autologous, allogous or allogeneic or xenogeneic tissue sources, for example, skeletal myocytes, cardiac myocytes or smooth muscle cells derived from line tissue, e.g. biopsy samples or from cultured cells. Alternatively, the biological component can include acellular tissue. Acellular tissue can be made illustratively by obtaining tissue sample harvested from a suitable donor, and then submersed in a balanced salt solution, such as Dulbecco's phosphate buffered saline. The disrupting of cell membranes then includes submersing the biological tissue sample in a solution including glycerol, whereas denaturing and removing intracellular proteins includes submersing the biological tissue in at least one detergent solution. The one or more detergent solutions can comprise ionic detergent solutions and nonionic detergent solutions. In some embodiments, the tissue sample can be submersed in a succession of ionic and nonionic solutions, where the ionic detergent solutions can include sodium deoxycholate or sodium dodecyl sulfate, and the nonionic detergent solutions can include TRITON® X-100. In addition, the acellular tissue sample is preferably rinsed with distilled water between each solution change. The resulting acellularized tissue construct can then be stored in a physiologic saline solution. Methods useful for the production and use of biological component comprising acellular tissue is described in Dennis, R. G., et al. U.S. Pat. No. 6,448,076, Ser. No. 09/896,651 issued Sep. 10, 2002 and is hereby incorporated herein in its entirety.

In some embodiments, the biological component can also include a matrix material that is prepared by forming a hydrogel scaffold and the like. The hydrogel scaffold can be made of any commonly known biocompatible hydrogel material, including hydrogels that are made from organic sources, including polysaccharides, polypeptide and proteins, and combinations thereof. In some embodiments, the hydrogel scaffold is then embedded with or mixed with a population of autologous, allogous or allogeneic or xenogeneic tissue constituents, for example, skeletal myocytes, cardiac myocytes or smooth muscle cells derived from live tissue, e.g. biopsy samples or from cultured cells. In addition to the hydrogel and cells, the biological component can also include one or more biologically active agents including: but not limited to, neural cell adhesion molecule (N-CAM), neuroglial CAM or NgCAM, TAG-1, contactin-2, myelin-associated glycoprotein (MAG), and deleted in colorecteal cancer protein (DCC); extra cellular matrix adhesion molecules: e.g. laminin, fibronectin, tenascin and perlecan; muscle and/or cell surface markers, e.g. cluster of differentiation markers (CD) molecules and combinations thereof, extra cellular matrix components, vitamins, minerals, drugs, medicaments, pharmaceutical compositions, amino acids, peptides, proteins, e.g. enzymes, antibodies, receptors, ion-ligand channels, glycoproteins, glycolipids, lipids, sterols, fatty acids, glycerides, nucleic acids including DNA, cDNA, RNA, mRNA, siRNA, shRNA, miRNA, polynucleotides, oligonucleotides, coding-gene sequences, non-coding genetic sequences and combinations thereof.

III) Conjugated Polymers

The conjugated polymer is a conducting (electrons or ions) coating (also known as conductive polymers), inter-connected network, or matrix that can be formed by electrochemical polymerization, chemical (oxidative or vapor deposition) polymerization, and in situ polymerization in a tissue or around cells or in a gel or scaffold or any combination thereof. The conjugated polymer can be deposited on a substrate using a variety of methods including but not limited to electrochemical deposition, evaporation, spin-coating, solvent-casting, chemical vapor deposition (CVD), layer-by-layer electrostatic interaction, electrostatic processing (electrospray/jetting/spinning), compressed air-spray, and atomization.

The term "conjugated polymer(s)" is used interchangeably with "conducting polymer(s)". Conjugated polymers are formed from their monomeric form via electrochemical polymerization, oxidative polymerization and other methods commonly used in the art. The conjugated polymer polymerized around an electrically conjugated substrate can also be referred to as a conducting polymer network due to its three dimensional, fuzzy, soft fibrils that extend out from the electrically conjugated substrate. In some embodiments, the conducting polymer network contains embedded biological components including cells, cellular constituents, bioactive molecules or substances and combinations thereof. In certain embodiments of the present technology, the conjugated polymers can be polymerized in the presence of dopants, tissue, cells, cell parts, cellular constituents, other bioactive molecules, viral, plasmid, yeast, dendromer, quantum dot, or micro-nano particle gene delivery vectors, and/or biodegradable micro-nano particles or fibers that are comprised of naturally-derived or synthetic polymers that may be decorated with surface functional groups or molecules intended for interaction with specific cells or molecules in the target effector tissue or may be employed for controlled-release delivery of one or more bioactive molecules, including, but not limited to, neural cell adhesion molecule (N-CAM), neuroglial CAM or NgCAM, TAG-1, contactin-2, myelin-associated glycoprotein (MAG), and deleted in colorecteal cancer protein (DCC); extra cellular matrix adhesion molecules: e.g. laminin, fibronectin, tenascin and perlecan; muscle and/or cell surface markers (CD) molecules and the like and combinations thereof contained within.

In some embodiments, the conducting polymers can include, but are not limited to: polythiophenes, poly(3,4-ethylenedioxythiophene) (PEDOT), poly(pyrrole), polyanilines, polyacetylenes, poly-3-hexylthiophene, melanins both natural and synthetic, poly (diallyldimethylammonium chloride), poly-4-vinylpyridine, poly(vinylalcohol), conjugated derivatives thereof, functionalized polymers thereof, polymer blends thereof and composites with the ability to conduct electronic charge or ions, and hybrid polymer-metal materials that are electrically or ionically conductive. Other conjugated polymers useful in the present technology can include functionalized copolymers made from EDOT and other conducting polymer derivatives, functional groups such as RGD, IKVAV, YIGSR peptides, and other functional groups that can be covalently attached to the conducting monomer, or they can be linked to spacers having bifunctional moieties that can be attach to the conjugated monomer used in making the conjugated polymer. A covalent attachment can be effected using any covalent chemistry known in the art, for example carboxylic functional attachment. Examples of preferred covalent attachment chemistries include amine, amide, ester, ether, and their heteroatom cognates, e.g., sulfonamide, thioether, and so forth. Typically, each pair of entities to be joined can jointly comprise a pair of reactive groups, such as a nucleophile and an electrophile, one respectively on each member of the pair. Where the biological entity (biomolecule, cell, cell fragment, organelle, or other biologically active molecule) is to be directly attached to the monomer or polymer, each will contain one reactive group of a pair. Where attachment is to take place through a linker, the linker will contain two reactive groups, one of which is capable of covalently reacting with a reactive group of the monomer and the other of which is capable of covalently reacting with a reactive group of the biological entity. The reactive group(s) can be already present as part of the monomer, linker, or biological entity, or it can be added thereto by reaction prior to performing the attachment reaction. Where attachment is to take place through a linker, the linker can be attached first to the polymer, first to the biological entity, or concurrently to both. Typically, the entities to be covalently attached can be suspended or dissolved in an appropriate solvent, e.g., aqueous methanol, aqueous ethanol, acetonitrile, dimethyl formamide, acetone, dimethyl sulfoxide, or a combination thereof, at an appropriate pH, commonly about pH 7 to about pH 10, and at a temperature from about 10° C. to about 40° C. A neutral-to-basic pH is typically used and this is in most cases provided by addition of a base to the reaction medium. Examples of preferred bases for this purpose include inorganic bases and organic nitrogenous bases. Among inorganic bases, metal hydroxides, carbonates, and bicarbonates are preferred, preferably alkali metal hydroxides, carbonates, and bicarbonates, and combinations thereof.

In some embodiments, conjugated polymers can also include non-conductive monomer or polymer that can be made conductive in the presence of an appropriate doping system. In some embodiments, conjugated polymers useful herein can also be chemically synthesized to contain functional side groups that can allow for binding of proteins, lipids and nucleic acids before or after polymerization. In addition to functionalization of the conducting polymers, bioactive molecules, including proteins, lipids and nucleic acids can be also attached to the conjugated polymers through hydrogen bonding, electrostatic and non-polar interactions. In some embodiments, the conjugated polymer is biodegradable and will dissolve in the presence of biological fluid, for example, when the device is implanted in situ e.g. implantable brain prostheses, neural stimulators, transient heart devices and the like. The biodegradable conjugated polymer can include, but are not limited to, polypyrrole, poly(3,4-ethylenedioxythiophene) (PEDOT) block PEG, and poly(3,4-ethylenedioxythiophene), tetramethacrylate and others which are commercially available from TDA Research Inc., Wheat Ridge Colo., USA.

Conjugated polymers contemplated by the present technology typically require counter ions for polymerization and electroconductivity across the electrode-tissue interface. The conjugated polymers are reached with a polyelectrolyte at the molecular level. Electron delocalization is a consequence of the presence of conjugated double bonds in the conducting polymer backbone. To make the conducting polymers electrically conductive, it is necessary to introduce mobile carriers into the double bonds, this is achieved by oxidation or reduction reactions (called "doping"). The concept of doping distinguishes conducting polymers from all other kinds of polymers. This process can be assigned as p-doping or n-doping in relation to the positive or negative sign of the injected charge in the polymer chain by analogy to doping in inorganic semiconductors. These charges remain delocalized being neutralized by the incorporation of counter-ions (anions or cations) denominated dopants. In certain embodiments, ionic electrolytes or dopants used to polymerize conducting polymers include but are not limited to: poly(styrene sulfonate) (PSS; Sigma Aldrich, St. Louis, Mo., USA), LiClO.sub.4, Phosphate-buffered saline (PBS; HyClone, Logan, Utah), Hank's Balanced Salt Solution (HBSS, HyClone), Collagen, Poly-D-Lysine (PDL), Poly-L-Lysine, poly-ornithine, and bioactive molecules of interest having the appropriate ionic charge for the type of doping system used and can include, but is not limited to: dexamethasone or other anti-inflammatory agents, antibiotics, anti-mitotics, growth factors, scar-reducing, poly acrylic acid, dodecylbenzene sulfonic acid (DBSA), p-toluenesulfonic acid (p-TSA) and combinations thereof. Methods for attaching linkers and other functional groups to the conjugated polymer useful in the methods of the present technology are disclosed in patent application Ser. No. 12/038,138 titled: "Carboxylic Acid-Modified EDOT For Bioconjugation" filed on Feb. 27, 2008, and methods for making and polymerizing conjugated polymers are disclosed in Martin et al., U.S. Patent Application Publication 2007/0060815 (Ser. No. 11/512,479) which are both incorporated herein in their entireties.

IV) Optional Housing Structures

An electrolyte composition can be included with the conjugated polymer and/or biological components to provide support and growth for growing neural cells and/or myocyte cells. In some embodiments, physiological and/or nutritive electrolytes (e.g. vitamins, minerals, carbon food sources, amino acids and the like) can be incorporated within the polymer, membrane, or hydrogel housing and/or the conjugated polymer component. Alternatively, the physiological electrolytes can be added separately to any one of the conjugated polymer component, the biological component and combinations of the two. Further the electrolyte fluid may be comprised of autologous serum-derived or naturally present electrolyte solution. In some embodiments, the physiological electrolytes can include any commonly known electrolyte compositions in dry or fluid form that is used for rehydration purposes.

B. Methods of Preparing and Using the Hybrid Bioelectrical Interface Device

In some embodiments of the present technology, the HBI device can include an abiotic construct operably connected electrically and/or ionically with conjugated polymer. The conjugated polymer can be prepared around the biological component and the abiotic component in several ways. In some embodiments, a substrate, for example, a polydimethylsiloxane (PDMS) film, sheet or strip can be sputtered on at least one surface with gold, forming a thin film. Upon the gold covered surface poly(3,4-ethylenedioxythiophene) (PEDOT) can be formed from monomers of EDOT. Methods for forming PEDOT covered surfaces are known in the art. Methods useful for forming PEDOT covered surfaces are described in Martin et al., U.S. Patent Application Publication 2007/0060815 (Ser. No. 11/512,479) which is incorporated herein in its entirety. However, other conjugated polymers described above can also be formed on the surface of the substrate. The PDMS sheet can be rolled up having the PEDOT facing the interior lumen of the rolled tube thereby forming a microtube housing. The microtube housing when implanted in vivo can have a first proximal end and a second distal end. As used herein, the proximal end is the end closest to the central nervous system and the distal end is the end closest the effector tissue, for example, the arm, hand, leg or foot musculature. The microtube housing can be filled with a biological component and the biological component can be linked to an abiotic component within one of the proximal or distal ends of the housing. An Illustrative method for forming the conjugated polymer component in the housing is shown in FIG. 4.

The HBI device can be used to provide a suitable target effector site for nerve structures that have been severed to form neuromuscular junctions as a treatment for neuropathy. In still other embodiments, the HBI device can be used to transmit physiologic motor action potentials in vivo and form a bioelectrical coupler for providing appropriate efferent prosthetic limb control and afferent prosthetic feedback. In order to provide such prosthetic limb control, the coupling of the nerve structures with the prosthetic limb requires that a closed loop sensory path be formed.

In some embodiments, the HBI device of the present technology electrically and ionically couples action potentials travelling via the nerves to an external electronic device capable of coordinating such action potential signals and converts these to limb motion. To construct a bidirectional hybrid bioelectrical interface, a peripheral nerve fascicle can be isolated from a nerve, and inserted into the proximal end of the HBI device housing, for example a microtube. The nervous tissue can be sutured or glued to the housing to anchor the fascicle within the housing. In some embodiments, the biologic component, for example, dissociated muscle cells (myocytes) can be housed inside the lumen of the housing. These cells release chemical signals which encourage peripheral nerve growth toward them. Inside the housing, axons will extend away from the fascicle and make contact with the myocytes. When an axon reaches a myocyte, it forms a neuromuscular junction and the myocyte begins to differentiate from a muscle precursor cell into a myotube. Eventually, many individual myotubes combine to form muscle tissue, which is then supported by the body. This muscle tissue will respond electrically to action potentials that come from the peripheral nerve fascicles as is propagated through the HBI device. The biological component upon which the muscle is created has been permeated with conductive polymer and should maintain its electrical connection to the electrode after the muscle forms. The electrode should record an average of the electrical activity from the tube lumen and muscle. Additionally, if current is passed through the electrode, it should stimulate the tube lumen and muscle, which will in turn stimulate any axon, which innervates the HBI device.

Figure 2:
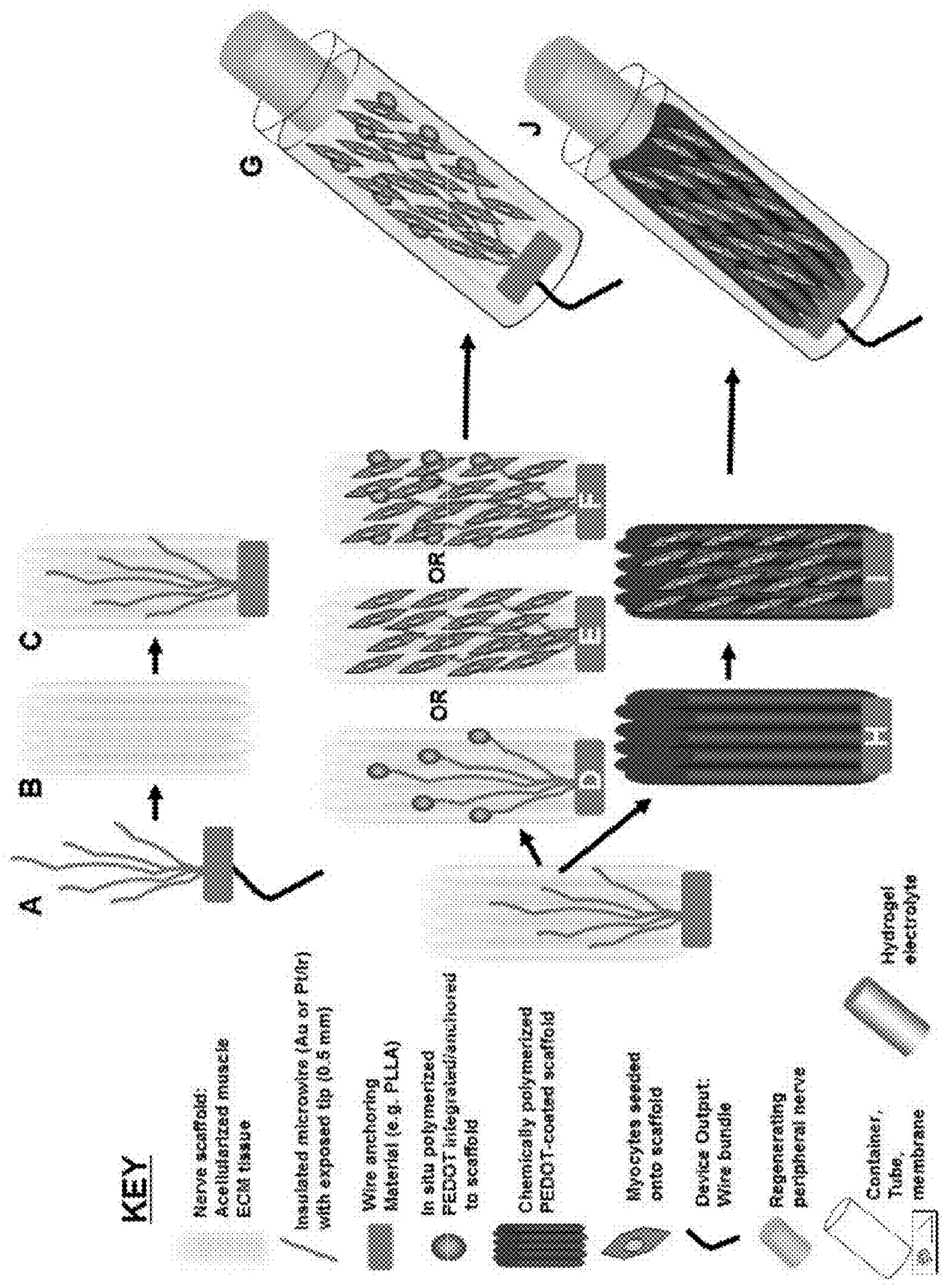
Figure 3:
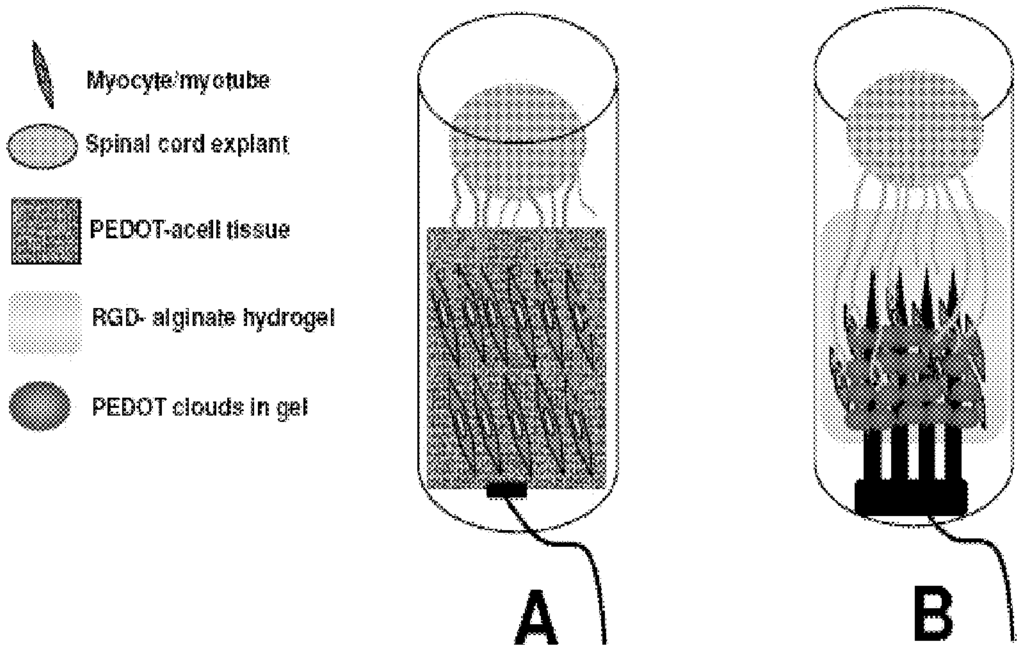
FIG. 3B depicts a schematic representation of a hybrid bioelectrical interface device having myocytes growing on the abiotic component and enveloped in PEDOT conjugated polymer. The myocytes and PEDOT are placed within a hydrogel scaffold providing a nutritive environment for the myocytes/myotubes.
Figure 6:
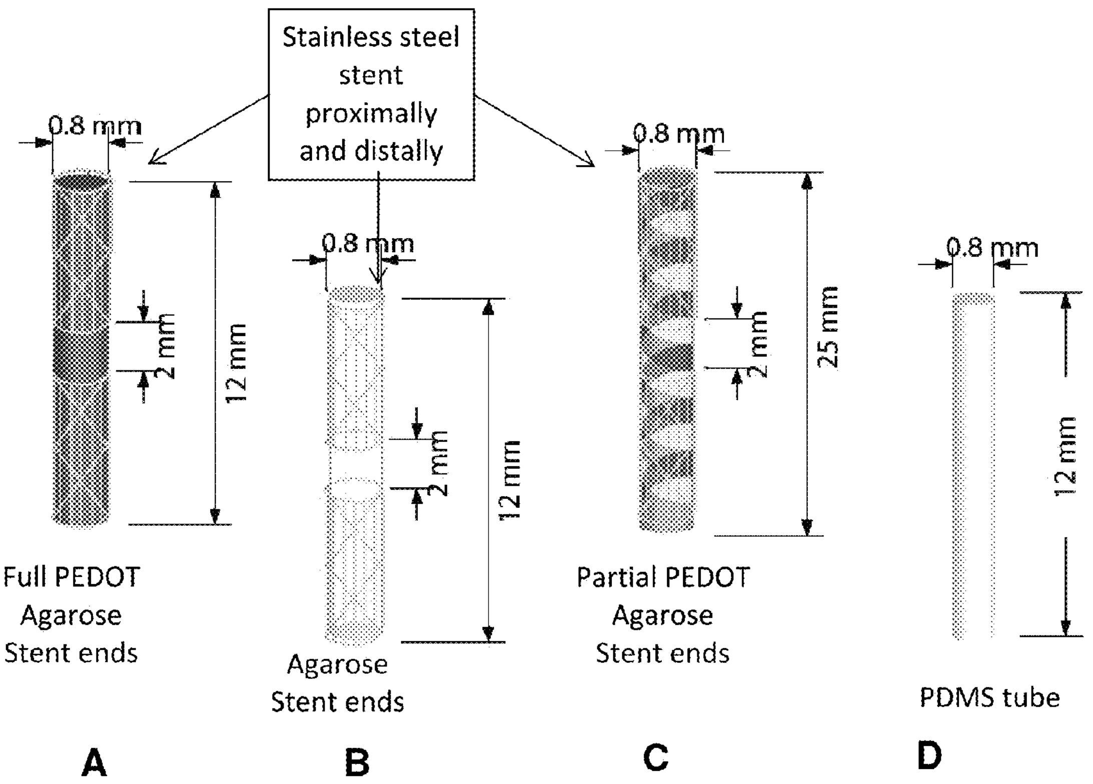

In some embodiments, the HBI device shown illustratively in FIG. 2, can be formed by providing an abiotic component consisting of a cluster of microwires connected to an external electronic device (EED) The biological component can be either an acellularized tissue scaffold or a naturally based hydrogel scaffold that is seeded with dissociated skeletal muscle cells, myocytes, or cardiac myocytes present in the biological component. The conjugated polymer component can include a PEDOT-coated acellularized tissue scaffold or in situ polymerized PEDOT that is polymerized directly within the either acellularized tissue scaffold or naturally based hydrogel scaffold seeded with living muscle cells. In some embodiments, the conjugated polymer can be polymerized randomly within and/or on the exterior surface of the biological component, arranged in a pattern within and/or on the exterior of the biological component, (for example a spiral pattern) or can be completely polymerized as a complete coating, substantially covering the biological component. The housing can include a hydrogel polymer, for example agarose, a tubular polymer membrane, which may be permeable to nutrients, or impermeable. (See FIGS. 4 and 5). The housing can also be filled with a hydrogel matrix which provides a source of electrolytes as well as a structural and nutritive support for the growth of muscle cells and the implanted nerve. In some embodiments, the housing can also have a rigid framework, for example, a stent or two or more stents disposed within the housing to provide the housing with support, especially if the housing is made from a hydrogel as shown in FIG. 6. Various orientations of the conjugated polymer within the housing are illustrated in non-limiting examples, as shown in FIGS. 6A-6D. In some embodiments, the proximal end of a single motor nerve fascicle can be inserted into the proximal end of the HBI container so that it contacts the biological component for example, muscle cells, and the conjugated polymer component of the device. The nerve can regenerate in a coordinated fashion within the HBI container and form synapses with the muscle cells (the natural target of the nerve) as well as possibly form synapse-like junctions (capacitive interface) with the PEDOT electrode component. The stability, viability and functional activities of the living cells (e.g. to form neuro-muscular junctions between the nerve tissue and myocytes) within the HBI device can also be facilitated by the presence of soluble biologically active agents (e.g. soluble drugs, nerve cell chemotactic agents, growth factors, cell adhesion molecules, e.g. neural cell adhesion molecule (N-CAM), neuroglial CAM or NgCAM, TAG-1, contactin-2, myelin-associated glycoprotein (MAG), and deleted in colorecteal cancer protein (DCC); extra cellular matrix adhesion molecules: e.g. laminin, fibronectin, tenascin and perlecan; muscle and/or cell surface markers (CD molecules) and the like) in the hydrogel. The interfaced wire-conjugated polymer electrode component of the HBI can serve as the electrical connection between the EED and the nerve allowing for "recording" of action potentials from the muscle cells and/or the nerve itself as well as making possible electrical stimulation of the muscle cells and nerve via the HBI.

In some embodiments, an in vivo construct can be used to determine conductive properties of a HBI device utilizing chemically polymerized PEDOT on a chemically acellularized biologic muscle scaffold. These in vitro constructs are illustratively shown in FIGS. 3A and 3B. In some embodiments, a HBI device can include a durable, high-fidelity, biologically integrated neural prosthetic interface that uses PEDOT-coated chemically acellularized muscle scaffolds (ACM) to detect the cortical synthesis of motor signals in the peripheral nervous system (PNS) in order to control robotic prosthetics. These materials do not possess cellular machinery necessary for action potential propagation and presumably conduct via electron mass transport. In this embodiment, composite abiotic-biotic constructs can be designed to match the 2-3 mm caliber of an adult rat peroneal nerve. There is no housing component in this in vitro embodiment. Biological component including animal derived acellular muscle scaffold and subsequent construct lengths can be manufactured to vary from about 2 mm to about 50 mm, within the predicted length range needed within an electronic interface device.

These composite constructs can be directly coapted both proximally and distally to viable rat hindlimb peroneal nerves immediately after nerve transaction, creating an interposition. The interface between the viable nerve and the composite construct is created through direct epineural coaptation of the nerve to the composite material. This technique allows the individual axons to come in direct contact with the polymer deposited on the composite construct. Charge transfer between the abiotic component in contact at least partially with a conjugated polymer, e.g. PEDOT and nerve is thus possible. There is a notable lack of directionality to this interface. The HBI device embodied in this version, through varied stimulation locations, can thus be used for both efferent neural signal detection and signal delivery. The proximal biotic component can be stimulated with recording signals within the construct, whereby the construct is "sensing" the biologic depolarizing current and acting as a probe, or recording wire. Furthermore, the recording can be performed distal to the construct altogether. The construct interposition will sense, propagate, and deliver biologic currents. Although this is not a proposed in vivo use (the distal nerve will eventually undergo Wallerian degeneration), it does allow in vivo construct conduction quantification. In some embodiments, stimulating the HBI device directly and measuring nerve conduction in the distal nerve, or using the HBI device as a stimulating wire can therefore be achieved. This embodiment creates a model necessary for in vivo stimulation parameter testing and optimization prior to construct use as a true afferent neural stimulator.

In some embodiments, the in vitro HBI device can be assembled in a cell culture dish in a liquid cell media. Furthermore, for in vitro studies, rather than the proximal end of a living nerve, the neural interface would be a nerve explant, dissociated neural cells, an organotypic slice culture, or some other form of explanted tissue or tissue-derived substance. Use of an in vitro model allows for more extensive testing and verification of success metrics, specifically verification of motor unit formation. These metrics include but are not limited to 1) electrophysiology: EMG recordings from muscle cells, 2) Histology: immunocytochemistry for acetylcholine receptor clustering (post-synaptic), change in agrin localization (pre-synaptic), phalloidin for actin cytoskeleton, 3) Chemical sensing: acetylcholine release detection (using PEDOT or AIROX sensing electrodes).

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

C. EXAMPLES

Example 1

In Vivo Use of an Hybrid Bioelectrical Interface Device

Methods And Materials

Animal Model: Experiments were performed using two month old, male, specific pathogen free F344 rats (Charles River Laboratory, Kingston, N.Y.). Biosynthetic Construct Preparation: ACM neural interface constructs were prepared from acellularization of whole F344 rat lower limb (Charles River, Wilmington, Mass.) vastus lateralis muscles. The acellular muscles were then dissected into bundles of several myofibrils under microscopic magnification using a Nikon SMZ-10A stereomicroscope (Nikon Instruments, Melville, N.Y., USA). These bundles had a maximum fiber length of 20 mm and a diameter of 2.0-3.0 mm (approximate dimensions of an intact rat peroneal nerve). These fibers subsequently underwent a single-cycle chemical PEDOT polymerization process using iron chloride (III) (Eq.1).

Eq. 1

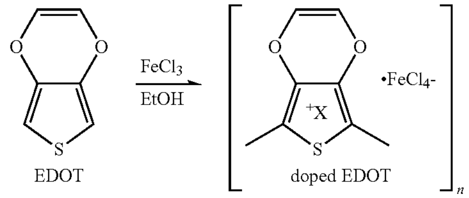

Experimental Groups: Electrophysiologic data was obtained in multiple experimental and control groups. Efferent peroneal nerve construct groups included 1) Acellular muscle (ACM)(n=10); 2) Acellular muscle chemically polymerized with EDOT using FeCl3 (ACM-PEDOT)(n=20); or 3) Acellular muscle after $FeCl_3$ treatment in absence of EDOT monomer (ACM-Fe)(n=10). Control groups included: 1) Intact peroneal nerve (Intact)(n=70); 2) Intact peroneal nerve treated with lidocaine (Intact-Lidocaine)(n=5); 3) Divided and repaired peroneal nerve, with no nerve graft (Epineural) (n=5); 4) Divided and repaired peroneal nerve gap using a nerve autograft (Nerve Graft)(n=20); and 5) Divided and unrepaired peroneal nerve (Nerve Gap)(n=20). Construct and gap lengths included 5 mm, 10 mm, 15 mm and 20 mm. Afferent sural nerve experimental groups included 1) 20 mm ACM-Fe (n=5); and 2) 20 mm ACM-PEDOT (n=5). Control groups included: 1) Intact sural nerve (Intact) (n=19); and 2) 20 mm nerve autograft (Nerve Graft) (n=5).

Operative Technique: Aided by a Zeiss operating microscope, 105 individual peroneal or sural nerve segments were resected from anesthetized live adult F344 rats (Charles River, Wilmington, Mass.) and the resultant nerve gap was acutely bridged using equivalent length biosynthetic constructs. The exposed proximal nerve, construct, and distal nerve were sequentially coapted using epineural 10-0 nylon monofilament sutures. The native nerve was stimulated proximal to the construct interposition and NCV and EMG measurements were obtained distally. To test conduction through the construct, this preparation exploits in vivo distal nerve segment excitability immediately after division, prior to Wallerian degeneration.

Electrophysiology: Customized TECA Synergy EMG station (Viasys Healthcare, Madison, Wis.) algorithms were used to deliver current and measure resultant compound muscle action potentials (CMAPs) in the EDL and antidromic Sensory Nerve Action Potentials (SNAPs) in the sural nerve. Measurements included amplitude, nerve conduction velocity (NCV) and latency in all groups.

Oxidative chemical PEDOT polymerization process employing iron chloride (III)—a mild, naturally present oxidizer was used to provide spontaneous, organized deposition on biologic substrates, including acellular muscle (ACM) which may avoid rejection common to all synthetic scaffolds. We used conventional clinical electrophysiologic measurements including nerve conduction studies (NCS) and electromyography (EMG) in a living rat to determine if PEDOT coated ACM interposition constructs (ACM-PEDOT) were bioelectrically relevant and could detect or deliver efferent (motor) nerve action potentials (see electrophysiological results shown in FIGS. 7A-9D). This single model, however, allows us to determine whether a biologic, non-immunogenic scaffold (ACM) coated with an electroconductive polymer (PEDOT), can enhance the electrical and ionic transport characteristics, detect an efferent action potential in a divided nerve, convert that action potential to an electronic signal, and facilitate transport of that signal to the remnant of a divided nerve to generate a physiologic action potential. Initially, to validate the experimental design and verify stimulator-originated nerve action potential generation in the native neural tissue, sodium channels (necessary to develop membrane potentials, and ultimately, nerve depolarization) were pharmacologically blocked in the intact nerve using Lidocaine. When 0.1 ml 1% lidocaine hydrochloride was applied directly to a 10 mm segment of intact peroneal nerve for 30 seconds, all electrophysiological responses measured at the extensor digitorum longus (EDL) muscle were eliminated. Absence of accessory or aberrant conduction pathways through serum or adjacent tissues was demonstrated by absence of any electrophysiological response in nerve segments distal to empty nerve resection sites (gaps) following proximal stimulation. ACM-PEDOT biosynthetic constructs were prepared by acellularizing, shaping, and treating the ACM fibers with a single-cycle chemical PEDOT polymerization process using $FeCl_3$.

Results And Discussion

The above described ACM-PEDOT containing HBI devices, conducted physiologic currents across interpositions of up to 20 mm—the maximum length tested. Efferent NCS/EMG results (shown in FIGS. 8A-8D) demonstrate ACM-PEDOT constructs conduct physiologic 0.53±0.19 mA (mean±SD) currents up to 20 mm with maximal resultant compound muscle action potential (CMAP) amplitude of 16.60±5.29 mV, (FIG. 8B) and latency of 1.09±0.15 ms (FIG. 8C). ANOVA with post-hoc analysis and post-hoc power analysis performed for each measured outcome demonstrated that ACM-PEDOT electrophysiologic parameters are not different from NCV/EMG values for intact nerve or from similar length nerve autografts ($p>0.05$, $\beta<0.2$). ACM-PEDOT constructs showed a statistical increase in conductive velocity (40.22±8.71 m/s) compared with intact nerve (22.15±3.68 m/s) ($p<0.05$). To determine conductivity contribution of the polymerization reagent iron chloride alone, we created constructs using the same chemical PEDOT deposition process, minus EDOT monomer. These ACM-Fe constructs were non-conductive. Likewise as an additional negative control, constructs created from ACM-alone were non conductive (data not shown). Unlike the millivolt electrical potentials observed in the muscular end organ of the peroneal nerve above, the sural nerve (purely sensory) relies upon microvolt sensory nerve action potentials (SNAPs) for signal propagation. These small signals pose a much greater challenge from a monitoring standpoint as technical factors and signal to noise issues assume greater importance. We tested whether ACM-PEDOT constructs were relevant in this setting by dividing the much smaller sural nerve, and repeating experiments described above, results shown in FIGS. 9A-9D. In this setting, 20 mm ACM-PEDOT constructs transmit discrete antidromic microvolt SNAP's with a mean amplitude of 35.78±27.56 μV and latency of 2.68±0.36 ms when stimulated with a 1.22±0.29 mA (FIG. 9B). ANOVA with post-hoc analysis performed for each measured outcome demonstrated that ACM-PEDOT performance does not differ from intact nerve (43.29±18.28 μV, 2.78±0.23 ms, 0.84±1.12 mA, respectively) ($p>0.05$, $\beta<0.2$), and outperforms 20 mm nerve autografts, which required more stimulation (8.08±3.22 mA) ($p<0.05$) leading to lower signal to noise ratio. ACM-PEDOT shows increased NCV (23.06±4.67 m/s) compared with intact nerve (16.38±1.35 m/s) ($p<0.05$). As previously demonstrated in the efferent motor action potential experiment, ACM, ACM-Fe, and nerve gaps were non-conductive. Chemically polymerized PEDOT-coated acellular muscle constructs can couple efferent motor action potentials and afferent sensory nerve action potentials in the distal end of a divided nerve to physiologic scale charge transport across an ACM-PEDOT biosynthetic construct with electrophysiologic parameters similar to intact peripheral nerve. It was also demonstrated that the signal conduction across the ACM-PEDOT construct has a greater velocity than intact nerve and is maintained over at least a 20 mm distance. Since signal conduction is distance-dependent, and since there is no conduction across longer constructs (10 mm, 15 mm, and 20 mm) in any of the control groups, including the acellular muscle scaffold alone, acellular muscle scaffold with iron, and the unreconstructed nerve gap, we speculate the ACM-PEDOT functions through a mass-transfer (ion) effect. The ability to connect these scaffolds to external monitoring equipment should make it possible to monitor axonal sprouting and regeneration following clinical or experimental nerve manipulations. The ability to apply an external electrical field could also be used to direct and enhance the rate and extent of neural regeneration.

Conclusion

Peripheral nerve efferent and afferent action potentials were detected and propagated in vivo using a hybrid bioelectrical interfacing device composed of PEDOT chemically deposited on biologically derived acellular muscle. The production, implantation, and in vivo electrophysiologic properties of these hybrid neural constructs and their ability to detect efferent (motor) action potentials proximally and deliver afferent (sensory) action potentials distally with electrophysiologic characteristics similar to intact peripheral nerve. It is possible that these electrically active biosynthetic scaffolds will make possible high resolution peripheral nerve interfaces necessary for next generation bionic arms and legs.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A hybrid bioelectrical interface device for interfacing living neural tissue with electronic devices comprising:

an abiotic component operable to transmit charge via electrons or ions;

a biological component interfacing with the neural tissue, said biological component comprising an acellularized tissue construct;

a conjugated polymer component interfacing said abiotic component and said biological component, said conjugated polymer component promoting electronic to ionic charge transfer between said abiotic and biological components; and a housing encapsulating at least a portion of said biological component, said conjugated polymer component and said abiotic component.

2. The hybrid bioelectrical interface device according to claim 1, wherein said housing comprises a rigid framework, a hydrogel, a permeable membrane, an impermeable membrane or a polymeric material.

3. The hybrid bioelectrical interface device according to claim 1, wherein said device further comprises one or more of an electrolyte, a biologically active agent and cells.

4. The hybrid bioelectrical interface device according to claim 1, wherein said abiotic component is selected from the group consisting of a wire, an electrode, an electrode array, a microelectrode array and a microelectromechanical system.

5. The hybrid bioelectrical interface device according to claim 1, wherein said conjugated polymer component comprises poly(3,4-ethylenedioxythiophene) (PEDOT), poly (pyrrole), polyanilines, polyacetylenes, poly-3-hexylthiophene, melanins, poly (diallyldimethylammonium chloride), poly-4-vinylpyridine, poly(vinylalcohol), polythiophenes, conjugated derivatives thereof, functionalized polymers thereof or polymer blends thereof.

6. The hybrid bioelectrical interface device according to claim 5, wherein said conjugated polymer component comprises poly(3,4-ethylenedioxythiophene) (PEDOT).

7. The hybrid bioelectrical interface device according to claim 1, wherein said biological component further comprises a material selected from the group consisting of: skeletal myocytes, cardiomyocytes, smooth muscle cells, extracellular matrix material (ECM) and combinations thereof.

8. The hybrid bioelectrical interface device according to claim 1, wherein said biological component is sourced from non-human tissue.

9. The hybrid bioelectrical interface device according to claim 1, wherein said acellularized tissue construct is an acellularized muscle scaffold (ACM).

10. An implantable hybrid bioelectrical interface device for interfacing living neural tissue with electronic devices comprising:

an abiotic component operable to transmit charge via electrons or ions;

a biological component interfacing with the neural tissue, said biological component being biologic, biologically-derived, or bio-functionalized;

a conjugated polymer scaffold interfacing said abiotic component and said biological component, said conjugated polymer scaffold promoting electronic to ionic charge transfer between said abiotic and biological components; and a housing comprising at least one of a stent, a permeable polymer tubular membrane, or an impermeable polymer tubular membrane, the housing further having an electrolyte, wherein said housing substantially surrounds at least a portion of said biological component, said conjugated polymer scaffold and said abiotic component.

11. The implantable hybrid bioelectrical interface device according to claim 10, wherein said abiotic component is selected from the group consisting of a wire, an electrode, an electrode array, a microelectrode array and a microelectromechanical system.

12. The implantable hybrid bioelectrical interface device according to claim 10, wherein said conjugated polymer scaffold comprises poly(3,4-ethylenedioxythiophene) (PEDOT), poly(pyrrole), polyanilines, polyacetylenes, poly (diallyldimethylammonium chloride), poly-4-vinylpyridine, poly (vinylalcohol), polythiophenes or polymer blends thereof.

13. The implantable hybrid bioelectrical interface device according to claim 12, wherein said conjugated polymer scaffold is $FeCl_4^-$ doped poly(3,4-ethylenedioxythiophene) (PEDOT), and said $FeCl_4^-$ doped poly(3,4-ethylenedioxythiophene) (PEDOT) is disposed within or around at least a portion of said biological component.

14. The implantable hybrid bioelectrical interface device according to claim 10, wherein said biological component comprises skeletal myocytes, cardiomyocytes, smooth muscle cells, acellularized tissue, extracellular matrix material (ECM) or combinations thereof.

15. A hybrid bioelectrical interface (HBI) device comprising:

an abiotic component operable to transmit charge via electrons or ions;

an acellularized tissue disposed at least partially on said abiotic component;

a conjugated polymer scaffold disposed at least partially within a biological component or at least partially covering said biological component; and a housing comprising a polymer or a hydrogel material, said housing having a proximal end and a distal end, said housing covering at least a portion of at least one of said abiotic component, said acellularized tissue and said conjugated polymer scaffold.

16. The hybrid bioelectrical interface device according to claim 15, wherein said acellularized tissue is an acellularized muscle scaffold (ACM).

* * * * *